(12) United States Patent
Houbolt et al.

(10) Patent No.: US 7,942,869 B2
(45) Date of Patent: May 17, 2011

(54) SKIN TREATMENT DEVICE WITH RADIATION EMISSION PROTECTION

(75) Inventors: Erik Houbolt, Drachten (NL); Jasper Zuidervaart, Drachten (NL); Mathijs Niehaus, Drachten (NL); Antonius Maarten Nuijs, Eindhoven (NL); Robbert Adrianus Maria Van Hal, Eindhoven (NL); Rieko Verhagen, Eindhoven (NL); Paul Anton Josef Ackermans, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 549 days.

(21) Appl. No.: 11/576,729

(22) PCT Filed: Sep. 30, 2005

(86) PCT No.: PCT/IB2005/053224
§ 371 (c)(1),
(2), (4) Date: Apr. 5, 2007

(87) PCT Pub. No.: WO2006/038168
PCT Pub. Date: Apr. 13, 2006

(65) Prior Publication Data
US 2008/0004611 A1    Jan. 3, 2008

(30) Foreign Application Priority Data
Oct. 5, 2004   (EP) .................................. 04104874

(51) Int. Cl.
*A61B 18/18* (2006.01)
(52) U.S. Cl. .................. 606/12; 606/9; 607/88; 607/91

(58) Field of Classification Search ............... 606/2–13; 607/88–94
See application file for complete search history.

(56) References Cited

U.S. PATENT DOCUMENTS

| 5,049,147 | A | * | 9/1991 | Danon ........................... 606/10 |
| 5,531,740 | A | | 7/1996 | Black |
| 5,653,706 | A | * | 8/1997 | Zavislan et al. ................... 606/9 |
| 5,995,867 | A | * | 11/1999 | Zavislan et al. ............... 600/476 |
| 6,174,325 | B1 | * | 1/2001 | Eckhouse ...................... 607/88 |

(Continued)

FOREIGN PATENT DOCUMENTS
WO    2000062700 A1    10/2000
(Continued)

*Primary Examiner* — Ahmed M Farah
(74) *Attorney, Agent, or Firm* — Sherry Womack

(57) ABSTRACT

The present invention relates to a skin treatment device (1, F). The device comprises a radiation source (13) in a housing, such that radiation can be emitted through an exit opening in the housing. It further comprises at least one skin presence sensor (43, 63) capable of measuring the presence of skin (7) in a number of respective positions, and a control unit (37). The control unit (37) is constructed to determine a covered portion of the exit opening (15) from a measurement signal of the skin presence sensor and to restrict emission of the radiation (13) to the covered portion of the exit opening (15), e.g. by modifying the control of a radiation beam manipulator (11), or by controlling radiation-blocking means, such as blinds, in the exit opening (15). The invention provides a more efficient and yet safe treatment device (1, 1'), since a larger exit opening (15) can be selected, while unwanted emission of radiation (13) through uncovered portions of the exit opening (15) is still prevented.

10 Claims, 3 Drawing Sheets

U.S. PATENT DOCUMENTS

Figure 1:
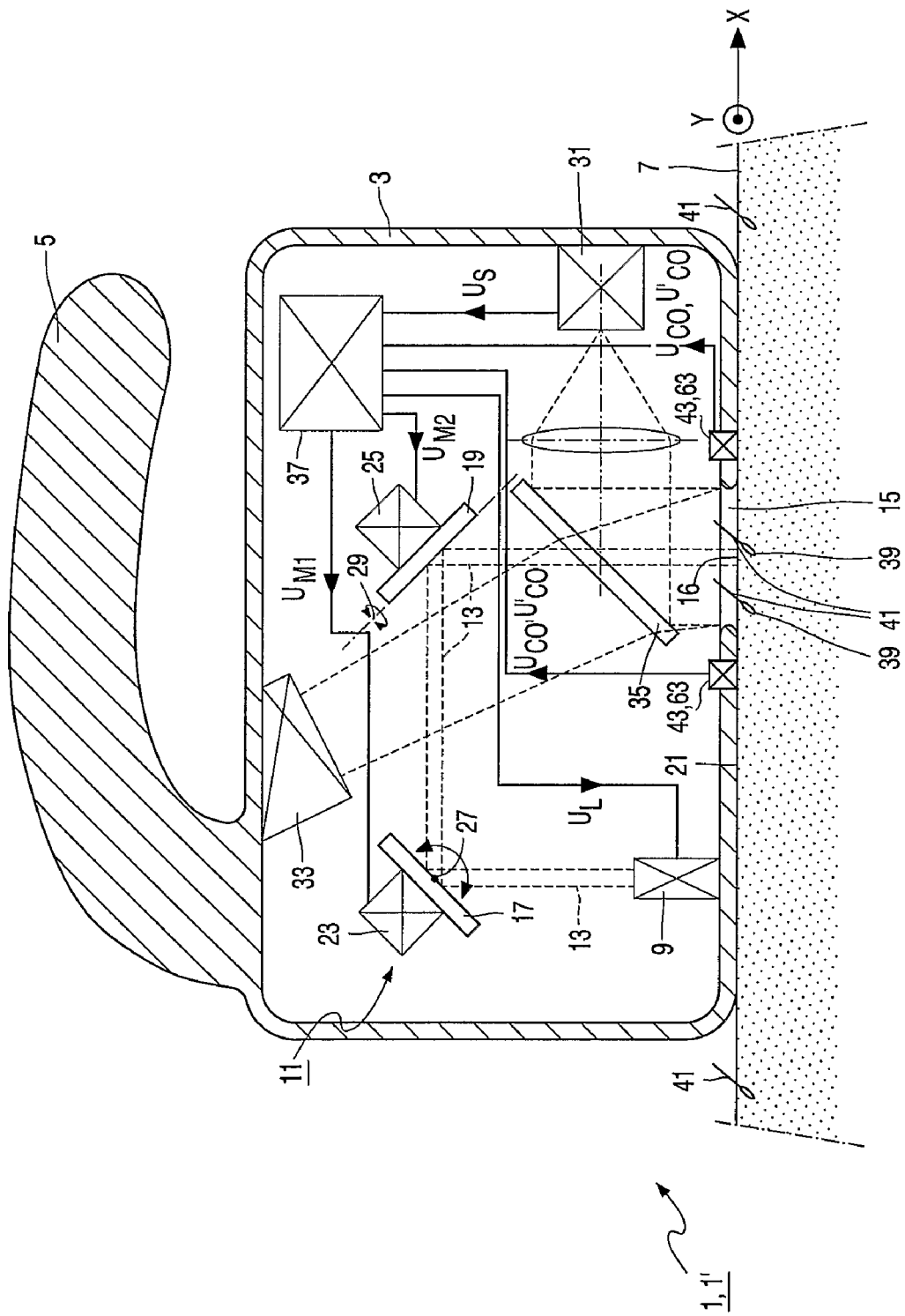

| | | |
|---|---|---|
| 7,101,365 B1 * | 9/2006 | Sharon .............................. 606/9 |
| 2002/0173781 A1 * | 11/2002 | Cense et al. ....................... 606/9 |
| 2003/0032950 A1 * | 2/2003 | Altshuler et al. ................. 606/9 |
| 2003/0036751 A1 * | 2/2003 | Anderson et al. ................. 606/9 |
| 2004/0176754 A1 * | 9/2004 | Island et al. ...................... 606/9 |

FOREIGN PATENT DOCUMENTS

| | | |
|---|---|---|
| WO | 02078559 A1 | 10/2002 |
| WO | 2002094116 A1 | 11/2002 |
| WO | 2004007022 A1 | 1/2004 |
| WO | 2004010884 A1 | 2/2004 |

* cited by examiner

SKIN TREATMENT DEVICE WITH RADIATION EMISSION PROTECTION

The present invention relates to a skin treatment device for treating skin by means of radiation, the device comprising a housing which accommodates a radiation source and which is provided with an exit opening for emitting the radiation, a detector system for detecting the presence of skin directly in front of the exit opening, said detector system comprising at least one skin presence sensor that is positioned near the exit opening and is capable of providing a sensor signal of a biophysical property by which the skin can be characterized, and a control unit which controls the emission of the radiation as a function of the sensor signal of the at least one skin presence sensor.

A device of the type mentioned in the opening paragraph is known from WO02/078559. The known device is a device for treatment of the skin that is used for e.g. hair removal. In the housing, a radiation source is arranged that, in operation, emits radiation through an exit opening. Around the exit opening one or more skin contact sensors are arranged that measure whether or not skin is present immediately in front of the exit opening. Only when all sensors indicate the presence of skin is the exit opening fully covered, so that a control unit is able to activate the radiation source. In other cases, i.e. when the exit opening is not fully covered, radiation could escape, which may be harmful to eyes, etc. Hence the radiation source is disabled by the control unit.

A drawback of this device is that it is not also very safe and efficient. For example, the control unit will disable the radiation source in a large number of cases in which the device is used on a surface that undulates strongly compared with the exit opening of the device, such as a human face. This is due to the exit opening not being completely covered in those cases. Especially in the case of a shaving device, its use on a face is common, but the irregular shape of a face prevents an efficient use of the device, while the presence of the eyes still requires a maximum radiation safety. A possible solution would be to make the exit opening much smaller, since this increases the relative flatness of the face in relation to the exit opening. However, this also lowers the efficiency of the device, since a small exit opening requires a large number of shaving motions by the user, while it is more difficult to treat every desired part of the skin with a reasonable amount of effort.

It is an object of the present invention to provide a device of the type mentioned in the opening paragraph which can be used more efficiently in more cases while still offering protection against unwanted emission of radiation.

To achieve this object, a device of the type mentioned in the opening paragraph, according to the invention, is characterized in that the control unit is constructed to determine from the sensor signal a covered portion of the exit opening that is covered by skin, and in that the control unit is constructed to restrict the emission of the radiation to at most said covered portion of the exit opening. In the device according to the invention, emission of radiation through the exit opening is limited to that portion of the exit opening which is covered by skin, so that emission of radiation is possible even in cases where the exit opening is not fully covered by skin. For example, if say 90% of the exit opening is covered by skin, the present device allows treatment of said 90%, whereas prior art devices would allow no treatment at all. For similar reasons it is now possible to use a larger exit opening. In prior art devices this could lead to longer treatment times, since the chance of the exit opening not being fully covered can only increase, thereby preventing treatment of the total surface area of the exit opening and causing a longer downtime of the radiation source. Contrarily, this latter circumstance is of no effect on the device of the present invention, since here the additional surface area of the exit opening will simply not be treated in as far as it is uncovered, causing a constant treatment time, while in cases where at least portion of the additional surface area of the exit opening is covered, this additional portion will indeed be treated at the same time.

Radiation safety is still ensured by restricting emission of radiation to the covered portion of the exit opening, which ensures that no direct radiation can escape. There will be only a minimal amount of escaping radiation, since this can only be due to radiation that has reflected off the skin, and in most cases only off a small part of the skin that is directed such that it allows reflected radiation to escape. Furthermore, this minimal amount of radiation is reflected radiation, which has lost a major portion of its energy by absorption in the skin. In addition, this reflected radiation will be diffuse radiation, since skin is a diffuse reflector, and diffuse radiation very quickly loses its intensity as a function of distance traveled. Specularly reflected radiation does not play a major role, since normally only a small portion of the radiation will be specularly reflected, e.g. on shiny skin. Furthermore, when radiation is specularly reflected with a small angle of incidence, i.e. almost perpendicularly, which is most often the case due to the rather limited range of angles of incidence in any practical apparatus, most of such radiation will be specularly reflected back into the apparatus. Only when e.g. a skin lobe or wrinkle is present, radiation may be specularly reflected away, and possibly into the outside world. However, this will only be a very narrow surface that will not be flat on a scale larger than a few millimeters. Hence most radiation will still be trapped, and the portion that is still able to escape is rather strongly divergent. In all, the probability of specularly reflected radiation escaping from the apparatus is not large, while the total power that could possibly cause any harm is even far, far less. Additionally, in the case of focused radiation, the radiation loses its intensity even more quickly.

At the basis of this invention lies the idea that it is not necessary to block the radiation source when the exit opening is not totally covered with skin for the above reasons. It is sufficient when emission of radiation is restricted to the covered portion, to prevent radiation from being emitted to the outside world directly. The particular way in which emission of radiation is restricted is not relevant to the invention, and hence not particularly limited. A number of possible advantageous measures therefor will be given below, at least some of which correspond to the dependent claims.

Note that the housing accommodates a source of radiation. This is intended to cover the case that an external radiation generator is used, the radiation of which is coupled into the housing by means of e.g. an optical waveguide. One could regard the exit opening of such a waveguide as the source of radiation, although it does not actually generate the radiation.

The expression "directly in front of" should be interpreted as denoting e.g. the presence of skin in contact with the housing adjacent or near the exit opening as well as covering the exit opening partly or completely. In principle, the skin presence sensor or sensors measure the presence of skin in front of themselves, upon the basis of which the detector system and/or the control unit determines the presence of skin in front of the whole or part of the exit opening. Regarding the number of skin presence sensors, it is preferred to use a plurality of sensors, e.g. at regular mutual distances. It is, however, also possible to use a single sensor, comprising a plurality of independently working segments.

In a particular embodiment of a device in accordance with the invention, the device further comprises at least one adjustable radiation-blocking means that is adjustable by the control unit to prevent emission of radiation through the exit opening outside the covered portion thereof. Such an adjustable radiation blocking means makes for a dynamic device, i.e. one that is able to dynamically adjust the effective exit opening to that portion that is actually covered by skin. Since the remaining, uncovered portion of the exit opening is effectively blocked from emitting radiation, this embodiment is inherently just as safe as a device with a static opening plus a skin contact sensor that switches off the radiation source when the exit opening is not fully covered.

Preferably, the adjustable radiation-blocking means is provided in or adjacent a plane of the exit opening. This ensures that no radiation can escape unwantedly, since radiation is either emitted onto skin that covers the exit opening, or is blocked by the adjustable radiation-blocking means. Alternatively, the radiation-blocking means may be provided, for example, in or on a mirror surface. Preventing unwanted light from being reflected may perform a similar function.

Advantageously, the adjustable radiation-blocking means comprise a moveable blind or diaphragm. The position of the blind(s) or diaphragm can be controlled, for example, by the control unit such that it corresponds to the uncovered portion of the exit opening. One or more blind or diaphragm drive means, such as electric motors or piezo-elements, may be provided for this purpose. One or more blinds may be preferable if the exit opening is rectangular, while a diaphragm may be more efficient with a more rounded exit opening, but all this also depends on the shapes of the body parts to be treated.

Another radiation-blocking means may be, for example, an electrochromic filter, the transmission of which may be locally influenced by means of a locally applied voltage, e.g. via thin, vapor-deposited electrodes. The control unit may then appropriately address those portions of said electrochromic filter that correspond to the uncovered portions of the exit opening, so that unwanted emission of radiation is prevented. Various other adjustable radiation-blocking means are within the scope of those skilled in the art, such as programmable mirrors, etc.

The device according to the present invention is described as having an exit opening. It goes without saying that the invention also relates to such devices with more than one exit opening, such as two exit openings.

In another advantageous embodiment of the device according to the present invention, the radiation source comprises a radiation beam source for supplying a radiation beam. The term "beam" herein indicates that radiation is emitted in a preferential direction, as opposed to diffuse or omnidirectional emission, cf. a torch light vs. an electric bulb. This offers the advantage that the radiation that is actually emitted through the covered portion of the exit opening is emitted in a preferential direction. Hence the amount of radiation that is emitted in a direction allowing undesirable escape through an uncovered portion of the exit opening is reduced.

Advantageously, the radiation beam is a focused beam, having a focus outside the housing in front of the exit opening. This ensures that any radiation that might still escape through an uncovered portion of the exit opening will be more or less strongly divergent, in particular if the focus position is selected to be (very) close to the exit window. This further enhances the safety of the device. Note, however, that a focusing element, or focusing in general, is not necessary, as the inherent safety of the device according to the invention is sufficient for most applications.

In a particular embodiment, the device further comprises an adjustable radiation beam manipulator for directing the radiation beam, which is supplied in operation by the radiation beam source, through the exit opening towards a target position on the skin to be treated, wherein the radiation beam manipulator is controllable by the control unit to restrict its directing of the radiation beam to the covered portion of the exit opening. In this embodiment, it is not the exit opening which is adjusted on the basis of the covered portion, as determined by the detector system, but rather the control of a supplied radiation is restricted to a desirable area, contrary to e.g. the laser shaving device as disclosed in WO02/078559, which is not controlled to a certain partial area of the exit opening.

In a particular embodiment, the radiation source comprises a flash lamp, providing radiation pulses of a desired wavelength, energy, and/or intensity. Such a flash lamp may be, for example, a gas discharge lamp. In another particular embodiment, the radiation source may comprise one or more LEDs, or a laser source. In all cases, the radiation may be in a beam or may be shaped into a beam, and it may preferably be shaped into a focused beam by means of optics such as a lens, a paraboloidal mirror, etc.

In a particular embodiment, the device comprises a window of a transparent material that covers the exit opening. This has an advantage in that it better defines the position of skin to be treated with respect to the radiation beam, in particular in the case of a focused beam. It furthermore offers the advantage that the skin is made substantially flat, at least in the covered portion. This ensures that most if not all of the radiation that is emitted onto the skin through the covered portion of the exit opening is (specularly) reflected back into the device, or is at the most diffusely scattered. In all such cases it will be easy to limit the amount of radiation that unintentionally leaves the device to an acceptable minimum.

In a particular embodiment of the invention, the detector system comprises at least two rows of skin presence sensors, one on each of two opposite sides of the exit opening. It is possible to determine the covered portion of the exit opening on the basis of measurement signals from the at least two rows of sensors. For example, a covered portion may be determined as follows, for a detector system having two rows on opposite sides of the sensor opening. In a first row, and starting from one end of this row, a number of neighboring sensors indicate "no skin present at this sensor". Next to these sensors, in the same row, another number of adjacent sensors indicate "skin present at this sensor", followed by yet another number of adjacent sensors, up to the opposite end of the row, which all indicate "no skin present at this sensor". In other words, there is one range of sensors that all indicate the presence of skin, which range is surrounded by two ranges indicating that no skin is present there. Likewise, in the opposite second row, such a range of adjacent sensors indicate the presence of skin, while end ranges of sensors indicate that no skin is present there. It will now be possible to determine the covered portion of the exit opening as that part that extends between the range of adjacent "skin present" sensors in the first row and the corresponding sensors in the second row, e.g. by drawing lines between the first and final sensors in these "skin present" ranges in the two opposite rows.

Alternatives to this method are of course possible. Many methods for this, determination are known per se in the art, and preferred embodiments will be disclosed and described below. Furthermore, more than one covered area may be possible. It may also be decided, either by an operator or a control unit with a program or algorithm, that there is actually no covered portion, e.g. since the "skin present" ranges in the two opposite rows are too far apart, indicating that e.g. two fingers partly cover the exit opening, etc. Moreover, it is possible that more than one covered portion is present, e.g. two fingers that both extend across the exit opening, and so on.

Preferably, the at least two rows each comprise at least three skin presence sensors, even more preferably a larger number, such as between five and one hundred skin presence sensors. It will be clear that a larger number of sensors offers a higher flexibility, for example for determining more than one covered area. Note that just two skin presence sensors in a row are not always sufficient to positively determine the presence of a continuous skin part in front of the exit opening. For example, two fingers with an opening between them may be placed in front of the exit opening, each finger contacting one sensor in each row. Positive sensor readings will now falsely indicate a fully covered opening. Although the same situation could also arise with more sensors per row and more fingers, normally the decreased distance from sensor to sensor ensures a higher safety against such misreadings. Therefore, preferably, an inter-sensor distance is less than the dimension of a predetermined skin detail, such as the width of a finger.

In a particular embodiment of the device according to the invention, the control unit is constructed to determine as a covered portion a portion of the exit opening that is bounded on a first side by a section of a first one of the two rows and on a second, opposite side by a section of a second one of the two rows, said sections each consisting of at least three adjacent skin presence sensors giving a measurement signal that skin is present. The control unit may then determine the covered portion of the exit opening according to principles known per se, such as those described here. Note that it is also possible to determine a covered portion as the portion bounded by at least two adjacent sensors in each row, or even by at least one sensor in a first row and at least two adjacent sensors in a second row. In a more general way, this relates to the case of a determination based on three sensors not in a straight line, the covered portion being formed by the triangle (or polygon) in between the three (or more) sensors that indicate the presence of skin. Note, however, that the risk of an incorrect determination is higher, since the portion determined as the covered portion could also be the only portion not covered by skin. The latter risk is much less, or even substantially zero, when three, or (many) more, sensor are used for such a determination.

To prevent an unwanted emission of radiation if, for example, an opening between two skin parts is present parallel to the rows, such as between two fingers that are each positioned along one of the rows, it is possible to additionally provide one or more skin presence sensors at at least one side substantially perpendicular to said at least two rows, e.g. along a third and fourth side of a rectangular exit opening.

Although the exit opening is preferably rectangular, it may also have a different shape, such as circular or ellipsoidal. It is again possible in such cases to discern opposite sides, although these are no longer strictly parallel. Note furthermore that the covered portion is generally determined as bounded by two lines intersecting the two rows of skin presence sensors and connecting corresponding first and last ones of the sensors that give a positive indication of the presence of skin. In other words, in each row there is a section with adjacent sensors that all indicate the presence of skin. Each such section has a first and a last sensor, seen in a predetermined direction. The two lines connect the respective first ones and the respective final ones. Preferably, though not necessarily, it is also possible to let the two lines extend substantially perpendicularly to the rows of sensors, or perpendicularly to an axis of symmetry of the exit opening, preferably a major axis of symmetry, in the case of an elongate exit opening. In such cases, a portion of the exit opening is only determined as covered if the sensors along both rows and along the same distance along the axis of symmetry indicate the presence of skin. In other words, the covered portion itself is taken to be symmetrical along the axis of symmetry. Although this is not necessary, as described above, this further increases the safety of the device.

The type of detector system or skin presence sensor is not particularly limited. In a particular embodiment of the device, the detector system comprises at least one of a physical pressure sensor, a gas pressure sensor, a gas flow sensor, and/or a heat conductivity sensor. Each such sensor may be used according to principles known to those skilled in the art. For example, the physical pressure sensor may be a piezoelectric element that provides an electrical signal upon being pressed, or a touch sensor with a relay etc., that makes or breaks an electrical contact upon being (com)pressed, etc.

A gas pressure sensor or a gas flow sensor may be used, for example, in a situation wherein a gas flow is maintained through openings in the housing around the exit opening. This may be brought about either by a supply of gas or by a supply of a vacuum. In either case the gas flow (or pressure) will suddenly change upon the sensor contacting the skin.

Both the above sensor types are not particularly suited to distinguish skin from other types of materials or objects. A heat conductivity sensor, which measures the heat conductivity of a material in contact therewith, is better in this respect, as skin has a heat conductivity within certain known ranges.

In a particular embodiment, the detection system comprises a plurality of electrically conducting contact sensors. Electrical sensors have the advantage that they are versatile: they may be used to measure a number of properties in dependence on the type of measuring instrument, such as resistivity, voltages phase changes, etc.

In particular, the detector system is constructed for measuring an impedance between a selectable pair of contact sensors. To achieve this, the detector system selects two contact sensors, e.g. one in each row, and measures the impedance between them. The measured impedance is very high whenever one or both contact sensors fail to contact the skin, practically infinite, whereas with both contact sensors contacting the skin the measured impedance is much lower, and indeed between certain known limits that depend inter alia on the condition of the skin (dry, moist, washed with soap, greasy, etc.) but also on whether there is a direct electrical path between the two sensors or whether such a path extends via other body parts. The latter may arise, for example, in the case of two different fingers each touching one of the two sensors. In such a case the measured impedance is much higher than with one finger touching both sensors, etc., owing to the longer electrical path length. Nevertheless, taking such circumstances into account, a reliable determination may be made on the basis of the measured impedance value. Such a determination is repeated for other pairs of contact sensors until a sufficiently reliable determination of the covered portion has been made. The routines for such a determination may be provided by a microcomputer, electronic circuitry, etc.

In another embodiment, the detector system of the device further comprises a counter electrode and is constructed for measuring an impedance between the counter electrode and a selectable one of the contact sensors. In this case, each pair of selected contact sensors consists of the counter electrode and one contact sensor that is freely-selected. This renders possible a better controlled and more constant measurement, but it is dependent on whether or not the counter electrode itself actually contacts the skin. For this purpose it is either possible to provide more than one counter electrode, one of which is selected for each set of measurements, or to select one of the contact sensors as the counter electrode for each set of measurements.

It may be advantageous to incorporate some of the impedance-measuring electrodes as transparent electrodes on a transparent window that covers the exit opening. This not only has the advantages as described above, such as a well-defined position of the skin with respect to the radiation, but also that the covered portion of the exit opening can be determined very reliably, since no interpretation of measuring signals of sensors around the exit opening needs to be made. Especially when combined with an electrochromic filter, a very precise and reliable device is obtained which is equally efficient with a radiation source and with a radiation beam source in principle.

In another advantageous embodiment of the device according to the invention, the at least one skin presence sensor is able to measure a scattering coefficient and/or an absorption coefficient of the skin for light of a predetermined wavelength. The presence of blood, water, cells, keratin, and melanin in human skin causes light to be absorbed and scattered in the human skin in a very characteristic way as a function of the wavelength of the light. Measuring the scattering coefficient and/or the absorption coefficient for light having a predetermined wavelength by means of said skin presence sensor leads to a very reliable determination of whether the medium that covers the exit opening is human skin. Details of this measurement are disclosed in WO02/078559, reference to which is hereby made.

In a particular embodiment, the detector system is provided with a plurality of light sensors and at least one light source for light of said predetermined wavelength, which at least one light source is arranged next to at least one of the light sensors and optically separated therefrom, the skin presence sensor determining the reflection coefficient by comparing an amount of light measured by the light sensor with an amount of light generated by the light source. As the light source is optically separated from the light sensor, the light originating from the light source cannot directly reach the light sensor. The light from the light source is capable of reaching the light sensor through scattering in the skin. In order to achieve that a substantial portion of the light from the light source reaches the light sensor through scattering in the skin, it is necessary that both the light source and the light sensor are in contact with the skin. Insufficient or no contact between the skin and the light source and/or the light sensor leads to a substantial reduction of the amount of light reaching the light sensor. Thus the skin presence sensor can reliably detect the value of the scattering coefficient and/or absorption coefficient, and in addition it is reliably detected whether the skin actually contacts the skin contact element.

A further embodiment of a device in accordance with the invention is characterized in that the detector system is provided with a further light source for light of a further, predetermined wavelength, which light source is also arranged next to at least one of the light sensors and is optically separated from said light sensors, the detector determining the scattering coefficient and/or absorption coefficient for both wavelengths by comparing the amounts of light measured by the light sensor with the amounts of light generated by the two light sources. Details of this particular measure, although employed in a different device as a whole, may be found in WO02/078559, reference to which is made here. In this further embodiment of the device according to the invention, the detector system determines the scattering coefficient and/or the absorption coefficient for two different wavelengths of the light. An even better characterization of the human skin is achieved by the values of the scattering coefficient and/or absorption coefficient for two different wavelengths of the light, whereby the reliability of the device is still further improved.

It may be important to define the condition of the skin during a measurement. For example, if additives such as a cooling gel or the like are used during a measurement of skin impedance, misleading measurements may result. Similar errors may be caused when a measurement of a reflection or scattering coefficient is performed. It will be advantageous to take such additives, and possible other circumstances such as skin temperature, perspiration, etc., into account. Alternatively, specific additives may be used to condition the skin. Certain oils, for example, may be used to make the top part of the skin (epidermis) more transparent to radiation. This ensures that the thickness and other properties of the epidermis, which may vary comparatively strongly among persons, and even between body parts, play a less important role.

A particular embodiment of a device in accordance with the invention is characterized in that at least one light source is a LED, and at least one light sensor is a photodiode. Said LED and photodiode are comparatively inexpensive and have small dimensions, so that the price and the dimensions of the skin presence sensor are limited, in particular if more or all light sources and light sensors are thus selected.

A further embodiment of a device in accordance with the invention is characterized in that the detector system is suitable for measuring a diffuse reflection coefficient of the skin for light of a predetermined wavelength. Owing to the presence of blood, water, cells, keratin, and melanin in human skin, light is diffusely reflected very characteristically by the human skin as a function of the wavelength of the light. A measurement of the diffuse reflection coefficient for light of a predetermined wavelength by means of the detector system reliably establishes whether or not the medium present directly in front of the exit opening is human skin.

A still further embodiment of a device in accordance with the invention is characterized in that the detector system is provided with a plurality of light sensors and a light source for light of said predetermined wavelength, which light source is arranged next to at least one of the light sensors and optically separated therefrom, the detector system determining the reflection coefficient by comparing an amount of light measured by each of the light sensors with an amount of light generated by the light source. As the light source is optically separated from the light sensors, the light from the light source cannot reach the light sensors directly. The light from the light source can reach the light sensors by reflection via the surface of the skin. The amount of light reaching the light sensors depends on the reflection coefficient and on the distance from the light source and the light sensors to the skin. In order to make sure that a predetermined amount of light from the light source reaches the light sensors by reflection, it is necessary on the one hand that the light is actually reflected by skin, i.e. the exit opening must actually be covered by skin, and on the other hand that a predetermined distance between the skin and the light source and between the skin and the light sensors must actually exist, e.g. by means of a spacer element. In this manner the skin presence sensor reliably detects whether the medium present directly in front of the exit opening is human skin.

Figure 2:
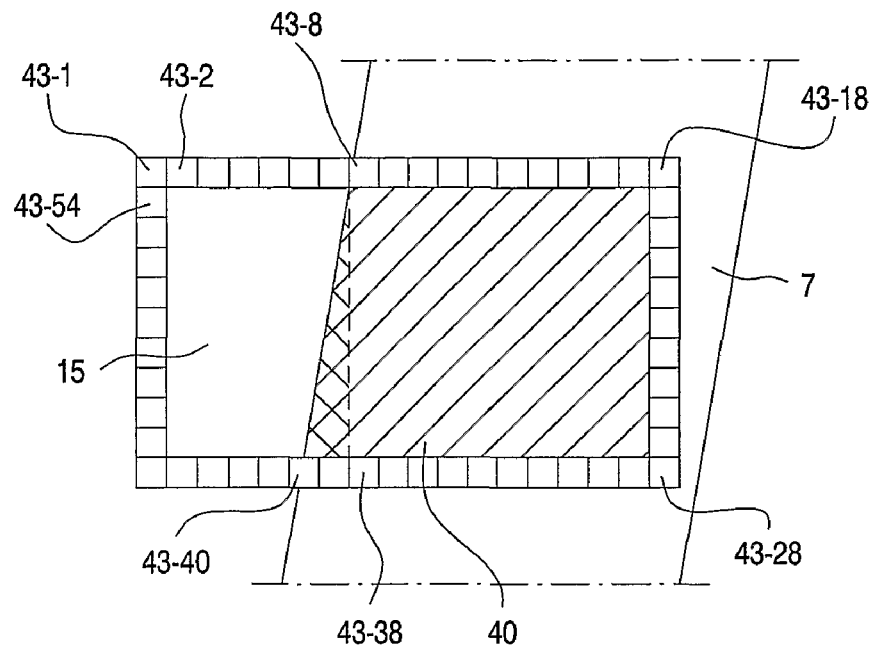
Figure 3:
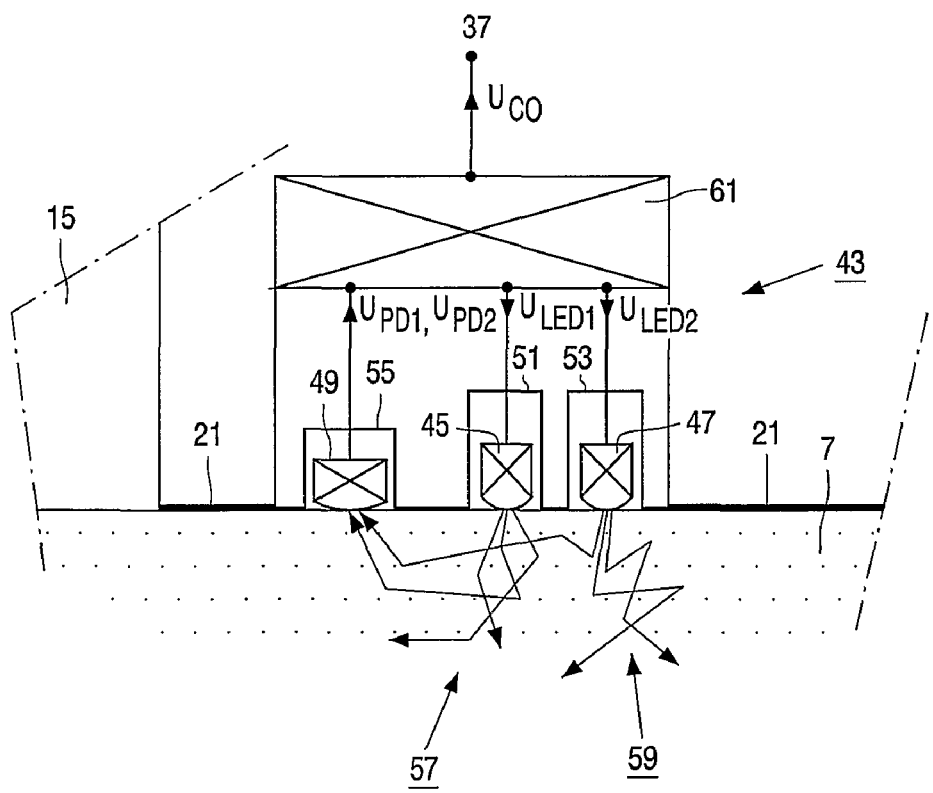
Figure 4:
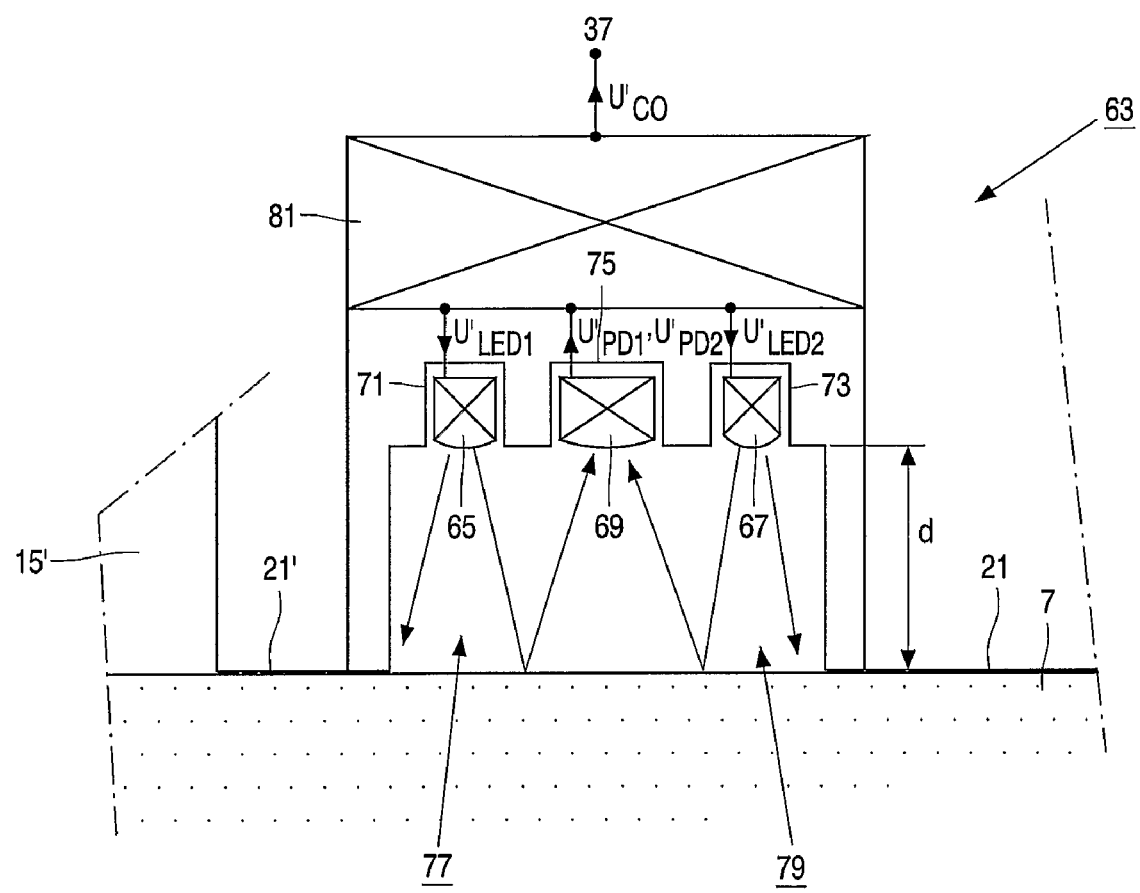

In the following, embodiments of a device in accordance with the invention are explained in detail with reference to the Figures, in which:

FIG. 1 diagrammatically shows a first embodiment of a device in accordance with the invention;

FIG. 2 diagrammatically shows an exit opening with a detector system of the device in accordance with FIG. 1;

FIG. 3 diagrammatically shows a skin presence sensor of the detector system shown in FIG. 2; and FIG. 4 diagrammatically shows a skin presence sensor of a second embodiment of a device in accordance with the invention.

FIG. 1 diagrammatically shows a first embodiment of a device 1 in accordance with the invention for treating skin by means of radiation, said device being a hair-removing device, in particular a laser depilation or shaving device, by means of which hairs present on the skin are removed for a comparatively long period of time, or even permanently, by means of laser light. Said device 1 comprises a housing 3 with a handle 5, so that the device 1 is portable and can be placed on or moved over skin 7 to be treated. The housing 3 accommodates a radiation source, in particular a laser source 9 such as a diode laser, and an adjustable laser beam manipulator 11 by means of which a—preferably focused—laser beam 13 generated by the laser source 9 during its operation can be positioned on the skin 7 in a target position 16 via an exit opening 15 provided in the housing 3. The exit opening 15 may be covered by a window (not shown) of a material that is transparent to the radiation used. In the example shown, the laser beam manipulator 11 comprises a first adjustable tilting mirror 17 and a second adjustable tilting mirror 19, which are both arranged at an angle of approximately 45° to a flat skin contact element 21 in which the exit opening 15 is situated and which forms a bottom wall of the housing 3 in the example shown. The tilting mirrors 17 and 19 can be tilted by means of a first actuator 23 and a second actuator 25 about a first tilt axis 27, which extends in the plane of the first tilting mirror 17 and is directed substantially parallel to the second skin contact element 21, and a second tilt axis 29, which extends in the plane of the second tilting mirror 19 and intersects the first tilt axis 27 substantially perpendicularly, respectively. The target position 16 of the laser beam 13 can be displaced over the skin 7 in a direction parallel to an X-direction and a Y-direction extending perpendicularly thereto, both directions being parallel to the skin contact element 21 in that the two tilting mirrors 17 and 19 are tilted.

To determine successive target positions, the device 1 is provided with an image sensor 31 in the example shown, such as a CCD image sensor or CMOS image sensor, which records an image of the portion of the skin 7 that is situated directly in front of the exit opening 15 by means of an auxiliary lamp 33 and a (dichroic) beam splitter 35. The device 1 further comprises a control unit 37 to which the image sensor 31 supplies an electrical signal $U_S$ which corresponds to the image recorded by the image sensor 31. The control unit 37 comprises a sensor by means of which, on the basis of the image recorded, the positions of the hair roots 39 of the hairs 41 present on said portion of the skin 7 are determined there. The control unit 37 controls the two actuators 23 and 25 by means of an electrical signal $U_{M1}$, and an electrical signal $U_{M2}$, respectively, such that the laser beam 13 is successively positioned in a series of target positions that correspond to the positions of the hair roots 39 thus determined. In each target position 16, the laser beam 9 is activated by the control unit 37 during a predetermined period of time and with a predetermined intensity by means of an electrical signal $U_L$, so that the hair roots 39 present are successively heated and are damaged or traumatized. Reference is made to WO-A-00/62700 for a detailed explanation of the operation of the device 1, which is only briefly described herein.

The laser beam 13 generated by the laser source 9 has a comparatively high intensity and hence is harmful when it contacts, for example, the eye. The device 1 in accordance with the invention is provided with means that can be used to prevent, to the extent possible, an emission of the laser beam 13 through a portion of the exit opening 15 that is not covered and enclosed by human skin, or is covered with a medium other than human skin, such as glass. The reliability of said means is very high, so that the device 1 in accordance with the invention is particularly suitable for use in the consumer market by inexperienced persons not skilled in the art.

As is shown in FIG. 1 and FIG. 2, said means comprise a detector system with a series of skin presence sensors 43 which are provided in the skin contact element 21 near the exit opening 15. In the example shown, said means comprise fifty-four skin presence sensors 43-1 through 43-54, which are arranged at small, regular distances from each other around the exit opening 15. Of course, any other number of sensors may also be suitably used, preferably arranged in at least two rows of preferably at least three sensors.

The sensors 43 can be suitably used to measure a biophysical property by which the human skin can be characterized. For example, said biophysical property is the impedance, the reflection coefficient, the scattering coefficient, and/or the absorption coefficient of the skin 7 for light of a predetermined wavelength.

FIG. 2 diagrammatically shows an exit opening with a detector system of the device in accordance with FIG. 1, partly placed over skin 7.

It can be seen that the skin 7 does not completely cover the exit opening 15. Skin presence sensors 43-1 through 43-7 and 43-41 through 43-54 give a negative signal, i.e. no skin present, while skin presence sensors 43-8 through 43-40 give a positive signal, i.e. skin present. Note that sensors 43-8 and 43-40 are borderline cases, the signals of which depend on the exact position of the border of the skin, their sensitivity and the predetermined limits with which to compare their signal.

In this example, the skin presence sensors 43 are impedance sensors. The sensors 43 each comprise an electrical contact which is to contact the skin 7. The control unit 37 (not shown in FIG. 2) is constructed to select two sensors from among the fifty-four, to which an electrical signal (e.g. a predetermined voltage signal of a known frequency) is applied. By measuring the response, in this case e.g. the current, the control unit is able to determine the impedance of the circuit comprising the two selected skin presence sensors. By subsequently comparing this result with values from a table stored in a memory, the control unit can determine whether the two skin presence sensors contact the skin, or whether one or two of the sensors do not contact the skin. For example, measured values of a few kΩ to about 100 kΩ at frequencies between about 50 Hz and 1 kHz are a sufficiently reliable indication that both sensors contact the skin, while values well above a few MΩ clearly indicate that there is no closed circuit. If both sensors indicate the presence of skin, this means that no further measurements need be performed for these sensors, apart from a control measurement. If, on the other hand, measurement signals indicate that at least one of the two sensors does not contact the skin, further measurements are required. By selecting one of the two previous sensors and combining this one sensor with one other sensor, a new set of two sensors is formed, with which the measurement procedure may be repeated. If a low impedance is measured now, it is established that both the other (new) sensor and the selected one of the original set of two sensors contact the skin, while at the same time it is established that the non-selected sensor of the original set of two sensors does not contact the skin. In this way, it is possible to determine whether or not a particular sensor contacts the skin.

The control unit 37 can thus determine which of the skin presence sensors 43-1 through 43-54 determine the presence of skin at their respective positions, i.e. if the values measured correspond to human skin characteristic values within predetermined limits.

The control unit can now determine the covered portion of the exit opening as the hatched area 40, bounded on one side by the dashed line, since all skin presence sensors that are adjacent that area 40 give a "skin present" signal. The cross-hatched area between the hatched line and the dotted line is also covered by skin, but since its exact position cannot be readily determined from the sensors signals originating from the borders of that area, it is safer to qualify it as "uncovered", although this is need not necessarily be the case. The remaining portion of the exit opening 15. i.e. to the left of the dashed line in FIG. 2, is thus determined as "uncovered" by the control unit 37. This uncovered portion should not be used as an exit opening for emitting the laser beam 13 of the device. To this end, the control unit 37 modifies the control of the laser beam manipulator 11 such that the tilting mirrors 17 and 19 direct the laser beam only through the covered (hatched) portion 40 of the exit opening 15. This may be done, for example, by limiting the respective ranges of deflection by the mirrors. If there are two or more unconnected covered portions, the control unit will still be able to modify the laser beam manipulator 11 to allow emission of the laser beam only through the covered portions.

An alternative embodiment of the device comprises radiation blocking means (not shown) that are able to block radiation outside the covered portion. To achieve this, moveable blinds are installed, preferably in the plane of the exit opening 15. Alternatively, an electrochromic filter controllable by the control unit is arranged in the exit opening 15.

As shown in the diagrammatic alternative embodiment of FIG. 3, the skin presence sensors 43 of the example shown each comprise two light sources 45, 47 for light having two different, predetermined wavelengths, in the example shown two LEDs, and a single light sensor 49, in the example shown a photosensor, which is arranged next to the light sources 45, 47. The light sources 45, 47 and the light sensor 49 are each arranged in a separate chamber 51, 53, 55 of the detector system, as a result of which the light sensor 49 is optically separated from the light sources 45, 47, i.e. light from the light sources 45, 47 cannot directly reach the light sensor 49. As is shown in FIG. 3, however, light beams 57, 59 from the light sources 45, 47 are capable of reaching the light sensor 49 through scattering in the skin 7. To make sure that a substantial portion of the light beams 57, 59 from the light sources 45, 47 can reach the light sensor 49, the light sources 45, 47 and the light sensor 49 must be in direct contact with the skin 7. The skin presence sensor 43 further comprises an electrical circuit 61 that successively activates the two light sources 45, 47 for a short period of time by means of two electrical signals $U_{LED1}$, and $U_{LED2}$. As a result, the circuit 61 receives two successive electrical signals $U_{PD1}$ and $U_{PD2}$ from the light sensor 49 which correspond to the amounts of light that the light sensor receives through scattering in the skin 7 from the two light sources 45 and 47, respectively. The circuit 61 subsequently determines the values of the scattering coefficient and/or the absorption coefficient of the skin 7 for the two different wavelengths of the two light sources 45, 47 by comparing the amounts of light received with the amounts of light generated by the light sources 45, 47, which amounts of light are given by the signals $U_{LED1}$ and $U_{LED2}$. The circuit 61 converts the values of the scattering coefficient and/or absorption coefficient thus measured into an electrical signal $U_{CO}$. As is shown in FIG. 1, the electrical signals $U_{CO}$ of all sensors 43 are received by the control unit 37 of the device 1. The control unit 37 comprises a comparator, not shown in the Figures, which compares the measured values of the scattering coefficient and/or absorption coefficient, etc., with values for the scattering coefficient and/or absorption coefficient, etc., that are characteristic of human skin and that are stored in a memory of the control unit 37. Note that an advantage of the light-based skin presence sensors over impedance-based sensors is that they can determine the presence of skin by themselves, without the need of an additional sensor (counter electrode).

As is shown in FIG. 3, the light sources 45, 47 and the light sensor 49 are arranged in the chambers 51, 53, 55, respectively, such that the light sources 45,47 and the light sensor 49 only contact the skin 7 if the skin contact element 21 contacts the skin 7 at the location of the relevant skin presence sensor 43, i.e. if there is no opening between the skin contact element 21 and the skin 7. This achieves that the skin presence sensors 43 can also detect whether the skin contact element 21 fully contacts the skin 7. If the skin contact element 21 is not in contact with the skin 7 at the location of one of the sensors 43, then the light sources 45, 47 and/or the light sensor 49 of the relevant skin presence sensor 43 are not in contact with the skin, as a result of which the amounts of light originating from the light sources 45, 47 and reaching the light sensor 49 are substantially reduced, and the values of the scattering coefficient and/or absorption coefficient measured by the light sensor will not correspond to the human skin characteristic values within the predetermined limits. The control unit 37 thereupon determines for all the skin presence sensors 43 whether or not they contact the skin. The control unit determines the covered portion of the exit opening from the result of this operation and, if necessary, modifies the control of the laser beam manipulator, a radiation blocking means (not shown), etc.

In this way, a very reliable protection of the device 1 is provided against accidental or deliberate emission of the laser beam 13 via uncovered portions of the exit opening 15. As a series of skin presence sensors 43 is used around the exit opening 15, the laser source 9 can only be directed through the covered portion of the exit opening 15. The laser source 9 cannot be activated if the device 1 is obliquely arranged on the skin 7 or at a short distance from the skin 7, because in such a case there will not be a sufficient number of adjacent skin presence sensors on at least two opposite sides of the exit opening 15 for the control unit to determine a covered portion of the exit opening. Furthermore, the laser source 9 cannot be activated if the medium present in front of the exit opening 15 is not human skin. In human skin, light is scattered and absorbed in a very characteristic way as a function of the wavelength of the light, which can be attributed to the presence of various components such as blood, water, cells, keratin, and melanin. The skin presence sensors 43 measure the values of the scattering coefficient and/or absorption coefficient for two different wavelengths of the light in the example shown: green light, which has a comparatively short wavelength, and red light, which has a comparatively long wavelength. The combination of the values of these coefficients for said two types of light is very specific in human skin, so that this enables human skin to be characterized in a substantially unique way. The skin presence sensors 43 can detect the presence of human skin against the skin contact element 21 with a very high degree of certainty. If the exit opening 15 is covered by a different medium, such as glass, transparent synthetic resin, or paper, the skin presence sensors 43 will detect different values for these coefficients, so that the control unit 37 cannot activate the laser source 9.

It is to be noted that instead of fifty-four skin presence sensors 43, a different number of skin presence sensors can be applied in the device 1. A reasonable degree of protection is already achieved if at least two skin presence sensors 43 are provided on opposite sides of the exit opening 15, which are arranged at some distance from each other near the exit opening 15, so that also a reasonable degree of protection is achieved in situations where the exit opening 15 is covered only partly. Preferably, the skin presence sensors 43 are arranged on all sides of the exit opening 15, such as in FIG. 2, in order to prevent an incorrect determination of the covered portion to the extent possible.

It is further noted that, instead of the skin presence sensors 43, it is alternatively possible to use skin presence sensors by means of which the scattering coefficient and/or absorption coefficient for only one value of the wavelength of the light is measured. As light is scattered and absorbed in a very characteristic way in the human skin as a function of the wavelength, a very reliable detection can already be achieved by carrying out a measurement at only one predetermined wavelength. The invention also comprises embodiments, however, in which the skin presence sensors carry out measurements for three or more values of the wavelength. It is further noted that the structure of the skin presence sensors 43 is simple, which can be attributed to the fact that the light sensor 49 is used for both light sources 45, 47. The invention also comprises embodiments, however, wherein a separate light sensor is used for each light source 45, 47, which light sensor, for example, is sensitive only to light of the wavelength of the associated light source. It is further noted that the two light sources 45, 47 in the skin presence sensor 43 are arranged on one side of the light sensor 49. This has the advantage that the light from the two light sources 45, 47 reaches the light sensor 49 by scattering of the light in the same portion of the skin 7, so that the accuracy of the skin presence sensor 43 is improved.

Acceptable results are also achieved, however, in an alternative embodiment of the device in accordance with the invention, wherein the light sources 45, 47 are arranged on both sides of the light sensor 49. The LEDs and photosensors employed in the skin presence sensors 43 are comparatively inexpensive and have small dimensions, so that the cost price and the dimensions of the skin presence sensors 43 are limited. The invention also comprises embodiments wherein a different type of light source and/or a different type of light sensor is employed in the skin presence sensors 43. It is further noted that the invention also includes embodiments wherein, unlike the example shown in FIG. 3, the circuits 61 do not form part of the skin presence sensors 43 or the associated detector system, but of the control unit 37.

As is shown in FIG. 1, a second embodiment of a device 1' in accordance with the invention is substantially identical to the above device 1 in accordance with the first embodiment. The device 1' differs mainly from the device 1 in that the device 1' is provided with skin presence sensors 63, instead of skin presence sensors 43, which skin presence sensors 63 are capable of measuring a reflection coefficient of the skin 7 with respect to light of a predetermined wavelength. Therefore, only the skin presence sensors 63 of the device 1' will be discussed in the following description, one of said skin presence sensors being diagrammatically shown in FIG. 4. As is shown in FIG. 4, the skin presence sensors 63 each comprise, in the example shown, two light sources 65, 67 for generating light of two different, predetermined wavelengths. In the example shown, said light sources are two LEDs. The skin presence sensor 63 further comprises a single light sensor 69, i.e. a photosensor in the example shown, which is arranged between the two light sources 65, 67.

The light sources 65, 67 and the light sensor 69 are each provided in a separate chamber 71, 73, 75, respectively, of the skin presence sensor 63, as a result of which the light sensor 69 is optically separated from the light sources 65, 67. As is shown in FIG. 4, light beams 77, 79 from the light sources 65, 67 can reach the light sensor 69 through reflection via the surface of the skin 7.

The skin presence sensor 63 further comprises an electrical circuit 81 which successively activates the two light sources 65, 67 for a short period of time by means of two electrical signals $U'_{LED1}$ and $U'_{LED2}$. As a result, the circuit 81 successively receives two electrical signals $U'_{PD1}$ and $U'_{PD2}$ from the light sensor 69, which electrical signals correspond to the amounts of light received by the light sensor 69 from the two light sources 65 and 67, respectively, through reflection via the skin 7. The circuit 81 subsequently determines the values of the reflection coefficient of the skin 7 with respect to the two different wavelengths of the light sources 65 and 67 by comparing the amounts of light received with the amounts of light generated by the light sources 65, 67, which amounts of light are given by the signals $U'_{LED1}$ and $U'_{LED2}$.

The circuit 81 converts the values of the reflection coefficient thus measured into an electrical signal $U'_{CO}$ which, as is shown in FIG. 1, is received by the control unit 37 of the device 1'. The control unit 37, which compares the measured values of the reflection coefficient with values stored in a memory thereof, which are characteristic of human skin, can only direct the laser source 9 to the covered portion of the exit opening 15, i.e. the portion for which the values as measured by the skin presence sensors 63 correspond to the human skin characteristic values within predetermined limits, i.e. the corresponding skin presence sensors 63 detect the presence of human skin. As light is reflected by the human skin in a very characteristic way as a function of the wavelength of the light, it is reliably determined by the skin presence sensors 63 whether the medium present directly in front of the exit opening 15 actually is human skin. In the example shown, this reliability is substantially further improved in that the skin presence sensors 63 measure the reflection coefficient for two different values of the wavelength, i.e. in this example for yellow light having a comparatively short wavelength and for red light having a comparatively long wavelength. As is shown in FIG. 4, the light sources 65, 67 and the light sensor 69 are at a predetermined distance d from the surface of the skin 7 only if the skin contact element 21 is in contact with the skin 7 at the location of the relevant skin presence sensor 63. The amounts of light received by the light sensor depend on the distance between the light sources 65, 67 and the skin 7 and on the distance between the light sensor 69 and the skin 7, and they decrease particularly substantially if the skin contact element 21 is not in contact with the surface of the skin 7, in which case an amount of light from the light sources 65, 67 can escape via the space present between the skin contact element 21 and the skin 7.

Therefore, in order to achieve that the values of the reflection coefficient measured by the skin presence sensors 63 correspond, within predetermined limits, to the human skin characteristic values, the exit opening 15 should preferably be covered by human skin as much as possible and, on the other hand, the skin contact element 21 should be in contact with the surface of the skin 7. It is noted, however, that the reliability with which the skin presence sensors 63 can determine the presence of the skin 7 against the skin contact element 21 is smaller than the reliability with which the skin presence sensors 43 of the device 1 can determine the presence of the skin against the skin contact element. It is further noted that the invention also comprises modifications of the skin presence sensors 63 and of the number and positions thereof, such as the modifications of the skin presence sensors 43 described above.

The skin presence sensors 43 and skin presence sensors 63 of, respectively, the device 1 and the device 1' in accordance with the invention as discussed above can be suitably used to measure the scattering coefficient and/or absorption coefficient of the skin, and the reflection coefficient of the skin, respectively. It is noted that the invention also comprises embodiments wherein use is made of a skin presence sensor which is suitable for measuring a different biophysical property by which the skin can be characterized, and wherein a comparator of the control unit can be suitably used to compare a value or condition of said property, measured by means of said skin presence sensor, with a skin characteristic value or condition of said property. An alternative biophysical property is, for example, the DC electrical resistance of the skin. This property is less reliable, however, than the properties described above because the electrical resistance of the skin is influenced by the presence of moisture and additives on the skin.

Another conceivable biophysical property is the presence of blood. The flow of blood in the skin is, for example, detectable by means of a laser-doppler measurement, and the resulting measuring signals are very characteristic of human skin. The sensors and processors necessary are more expensive, however, than the light sources and light sensors used in the skin presence sensors 43 and 63 discussed above. Other techniques suitable for use in a device in accordance with the invention for detecting the presence of skin are skin-imaging techniques, such as optical coherence tomography, confocal microscopy, ultrasound, two-photon microscopy, and spectroscopic techniques. These techniques are very reliable, but owing to their complexity they are less suitable for use in devices for the consumer market and more suitable for use in devices for the professional market.

The devices 1 and 1' in accordance with the invention as discussed above are laser depilation devices. The invention, however, also comprises other types of hair-removing devices, wherein hairs are shortened or removed by means of radiation issuing from an exit opening. An example of such a hair-removing device is a laser shaver. The operation of such a laser shaver is basically the same as that of the above laser depilation devices, however, the target position of the laser beam is not in the hair root but in a position on the hair just above the surface of the skin. Another type of hair removing device to which the invention may be applied is, for example, an IPL (intense pulsed light) depilation device.

The devices 1 and 1' discussed above all are hair-removing devices. It is noted that the invention also comprises other types of devices for treating the skin by means of radiation. Examples of such devices are devices for the medical treatment of skin by means of radiation, such as by means of laser light, flashlights, or other types of radiation having a comparatively high intensity. Such devices are used, for example, for treating birthmarks, such as naevus pigmentosus and naevus vinosus, present on the skin, psoriasis, acne, and wrinkles, or aberrations of blood vessels present in the skin. Other examples of such devices include devices for skin rejuvenation cures by means of radiation.

It is finally noted that the invention also comprises devices wherein the skin presence sensor or skin presence sensors are arranged in a position that differs from their position in the skin contact element of the present device. A position of the skin presence sensors in the skin contact element near or inside the exit opening, as in the devices 1 and 1' discussed above, however, generally leads to an optimum protection of the device.

The invention claimed is:

1. A skin treatment device for treating skin through the use of radiation, the device comprising a housing which accommodates a radiation source and which is provided with an exit opening for emitting the radiation,
   a detector system for detecting the presence of skin directly in front of the exit opening, said detector system comprising at least one skin presence sensor that is positioned near or in the exit opening and is configured to provide a sensor signal of a biophysical property by which the skin can be characterized, and
   a control unit which controls the emission of the radiation as a function of the sensor signal of the at least one skin presence sensor,
   wherein the control unit is constructed to determine from the sensor signal a covered portion of the exit opening that is covered by skin, wherein the covered portion is less than an entire area of the exit opening, and in that the control unit is constructed to restrict the emission of the radiation to at most said covered portion of the exit opening such that emission of radiation is possible even in cases where the exit opening is not fully covered by skin.

2. A device as claimed in claim 1, wherein the radiation source comprises a radiation beam source for supplying a radiation beam, wherein the device further comprises an adjustable radiation beam manipulator for directing the radiation beam, supplied by the radiation beam source during its operation, through the exit opening towards a target position on the skin to be treated, and wherein the radiation beam manipulator is controllable by the control unit so as to direct the radiation beam exclusively to the covered portion of the exit opening.

3. A device as claimed in claim 1, wherein the detector system comprises at least two rows of skin presence sensors, one on each of two mutually opposed sides of the exit opening.

4. A device as claimed in claim 3, wherein the at least two rows each comprise at least three skin presence sensors.

5. A device as claimed in claim 3, wherein the control unit is constructed to determine as a covered portion a portion of the exit opening that is bounded on a first side by a section of a first one of the two rows and on a second, opposite side by a section of a second one of the two rows, said sections each consisting of at least three mutually adjoining skin presence sensors giving a measurement signal indicating that skin is present.

6. A device as claimed in claim 1, wherein the detector system comprises at least one of a physical pressure sensor, a gas pressure sensor, and a heat conductivity sensor.

7. A device as claimed in claim 1, wherein the detection system comprises a plurality of electrically conducting contact sensors.

8. A device as claimed in claim 7, wherein the detector system is constructed for measuring an impedance between a selectable pair of the contact sensors.

9. A device as claimed in claim 7, further comprising a counter electrode, wherein the detector system is constructed for measuring an impedance between the counter electrode and a selectable one of the contact sensors.

10. A device as claimed in claim 1, wherein the at least one skin presence sensor is capable of measuring a scattering coefficient, an absorption coefficient, and a reflection coefficient of the skin with respect to light of a predetermined wavelength.

* * * * *